US010974226B2

(12) United States Patent
Schucker et al.

(10) Patent No.: US 10,974,226 B2
(45) Date of Patent: Apr. 13, 2021

(54) CATALYTIC PROCESS FOR OXIDATIVE COUPLING OF METHANE

(71) Applicant: SABIC Global Technologies B.V., Bergen op Zoom (NL)

(72) Inventors: Robert C. Schucker, Sugar Land, TX (US); Pankaj S. Gautam, Sugar Land, TX (US); Katarzyna Derrickson, Sugar Land, TX (US); Hoang Nguyen, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/579,024

(22) Filed: Sep. 23, 2019

(65) Prior Publication Data

US 2020/0094223 A1 Mar. 26, 2020

Related U.S. Application Data

(60) Provisional application No. 62/735,379, filed on Sep. 24, 2018.

(51) Int. Cl.
| | |
|---|---|
| *B01J 23/00* | (2006.01) |
| *C07C 2/84* | (2006.01) |
| *B01J 37/08* | (2006.01) |
| *B01J 37/02* | (2006.01) |

(52) U.S. Cl.
CPC .......... *B01J 23/005* (2013.01); *B01J 23/002* (2013.01); *B01J 37/0215* (2013.01); *B01J 37/08* (2013.01); *C07C 2/84* (2013.01); *C07C 2523/10* (2013.01)

(58) Field of Classification Search
None
See application file for complete search history.

(56) References Cited

U.S. PATENT DOCUMENTS

| | | | | |
|---|---|---|---|---|
| 5,041,407 A | * | 8/1991 | Williamson | ......... B01D 53/945 423/213.5 |
| 5,321,185 A | * | 6/1994 | van der Vaart | ......... C07C 2/84 585/500 |
| 6,087,545 A | | 7/2000 | Choudhary et al. | |
| 6,566,573 B1 | | 5/2003 | Bharadwaj et al. | |
| 7,008,560 B2 | | 3/2006 | Ramani et al. | |
| 2002/0091064 A1 | * | 7/2002 | Nakamura | ........... B01D 53/945 502/302 |
| 2006/0060826 A1 | * | 3/2006 | Atanackovic | ........ G02B 6/1225 252/500 |
| 2007/0209580 A1 | * | 9/2007 | Kondo | .................... C30B 23/00 117/204 |
| 2008/0295879 A1 | * | 12/2008 | Atanackovic | ......... H01L 37/025 136/238 |
| 2009/0010815 A1 | * | 1/2009 | Murata | ................ B01J 37/0246 422/171 |
| 2012/0228634 A1 | * | 9/2012 | Sugi | ..................... H01L 29/7803 257/77 |
| 2013/0115144 A1 | * | 5/2013 | Golden | ................ B01J 37/0036 422/170 |
| 2014/0011667 A1 | * | 1/2014 | Tomita | .................. C04B 35/565 502/69 |
| 2014/0166980 A1 | * | 6/2014 | Goda | ...................... H01L 33/32 257/13 |
| 2014/0273418 A1 | * | 9/2014 | Cheng | ............... H01L 29/78603 438/479 |
| 2015/0258483 A1 | * | 9/2015 | Kikuchi | .............. C04B 38/0016 428/117 |
| 2017/0040499 A1 | * | 2/2017 | Ushiyama | ............. H01L 33/502 |
| 2017/0057875 A1 | * | 3/2017 | Ishizuka | ............. C04B 35/6261 |
| 2017/0122161 A1 | * | 5/2017 | Fukami | ................. F01N 3/2803 |
| 2017/0263528 A1 | * | 9/2017 | Yoshida | ............. H01L 29/2003 |

FOREIGN PATENT DOCUMENTS

| | | | |
|---|---|---|---|
| JP | 6308998 | | 4/2018 |
| WO | 2015137270 | * | 9/2015 |
| WO | WO 2018/078567 | | 5/2018 |

OTHER PUBLICATIONS

Wang, et al. "Porous silicon carbide as a support for Mn/Na/W/SiC catalyst in the oxidative coupling of methane," *Applied Catalysis A: General*, 2017, 537:33-39.

* cited by examiner

*Primary Examiner* — Sheng H Davis
(74) *Attorney, Agent, or Firm* — Norton Rose Fulbright US LLP

(57) ABSTRACT

Supported oxidative coupling of methane (OCM) catalysts, methods of making the catalysts, and uses thereof are described. A supported OCM) catalyst can include a nonporous inert support having a high thermal conductivity and an OCM mixed metal oxide material in contact with surface of the nonporous inert support.

20 Claims, 7 Drawing Sheets

CATALYTIC PROCESS FOR OXIDATIVE COUPLING OF METHANE

CROSS REFERENCE TO RELATED APPLICATIONS

This application claims the benefit of priority of U.S. Provisional Patent Application No. 62/735,379 filed Sep. 24, 2019, which is hereby incorporated by reference in its entirety.

BACKGROUND OF THE INVENTION

A. Field of the Invention

The invention generally concerns supported oxidative coupling of methane (OCM) catalysts, methods of manufacture, and uses thereof. The supported OCM catalyst can include a nonporous inert support having a high thermal conductivity and an OCM mixed metal oxide material in contact with the surface of the nonporous inert support.

B. Description of Related Art

Methane can be used to produce ethane and/or ethylene through the oxidative coupling of the methane (OCM) reaction. While extensive research and development has been devoted to this reaction, the reaction largely remains inefficient on a commercial scale. One of the key challenges is the high reaction temperature (typically greater than 750° C.) required to make the reaction proceed. The need for such a high temperature is due to the bond strength (bond dissociation energy) of the tetrahedral C—H bonds in methane, which is 104 kcal per mole (kcal/mol). This C—H bond strength makes methane less reactive and difficult to undergo oxidative conversion to form ethylene.

The oxidative coupling of the methane is represented by the following equations:

$$2CH_4 + O_2 \rightarrow C_2H_4 + 2H_2O \quad \Delta H = -67.4 \text{ kcal/mol} \quad (I)$$

$$2CH_4 + \tfrac{1}{2}O_2 \rightarrow C_2H_6 + H_2O \quad \Delta H = -84.6 \text{ kcal/mol} \quad (II)$$

As shown in Equations (I) and (II), oxidative conversion of methane to ethylene or ethane is exothermic. It should be noted that the heats of reaction for Equations (I) to (II) and (III) to (IV) below are given per mole of oxygen consumed. Excess heat produced from these reactions can push conversion of methane to carbon monoxide and carbon dioxide rather than the desired $C_{2+}$ hydrocarbon product:

$$CH_4 + 1.5O_2 \rightarrow CO + 2H_2O \quad \Delta H = -82.8 \text{ kcal/mol} \quad (III)$$

$$CH_4 + 2O_2 \rightarrow CO_2 + 2H_2O \quad \Delta H = -95.9 \text{ kcal/mol} \quad (IV)$$

The excess heat from the reactions in Equations (III) and (IV) further exacerbate this situation, thereby substantially reducing the selectivity of ethylene production when compared with carbon monoxide and carbon dioxide production.

Problems associated with gas phase heterogeneous OCM catalysis includes the activation of $CH_4$ on a metal oxide surface and gas phase free-radical chemistry. Ethane and/or ethylene is produced mainly by the coupling of the surface-generated $.CH_3$ radicals in the gas phase. The yield of $C_2H_4$ and $C_2H_6$ can be limited by secondary reactions of the $.CH_3$ radicals with the surface of the catalyst and by the further oxidation of $C_2H_4$, both on the catalyst surface and in the gas phase. It is desirable to maximize the surface area of the catalyst to limit side reactions and promote formation of ethylene. Reduction in particle size into the nanoparticle size range can be used to achieve maximum surface area. Unfortunately, the use of nanoparticulate catalysts has several drawbacks: (1) they cannot be used in a typical fixed bed reactor, even of reduced bed height, as they will be easily carried away and lost from the process; and (2) even the use of a packed bed of 10 to 15 mm in height results in a significant increase in pressure drop across the bed and concomitant decrease in selectivity to the desired product (ethylene). As discussed above, removal of heat from the OCM reactor is critical. However, normal catalyst supports have very low thermal conductivity and are not suitable for this application.

Attempts to improve the catalysts for OCM processes include wash-coating small catalyst particles onto microporous monoliths made from cordierite or silicon carbide or onto nonporous metallic supports such as an iron-chromium (FeCr) alloy metal monoliths. Attempts to "glue" the catalyst in place using alumina or other cements have been performed. All these attempts suffer in decreased activity, leaching of the catalyst from the support, and inefficient methodology to produce the catalyst. Other attempts to improve the stability and/or performance of the OCM catalyst include the use of silicon carbide (SiC) as a support material. By way of example, U.S. Pat. No. 7,008,560 to Ramani et al. describes a process to produce synthesis gas hydrogen ($H_2$) and carbon monoxide (CO) using a catalytic metal oxide supported on porous SiC support material. Under the synthesis gas conditions, no coupling of methane was observed. In another example, U.S. Pat. No. 6,087,545 to Choudhary et al. describes a mixed strontium and other alkaline earth oxides deposited on a sintered low surface porous catalyst carrier that can be a mixture of SiC and other components and have a porosity of 43%. These catalysts resulted in a 10 to 18% conversion of methane with a selectivity to $C_{2+}$ of greater than 73% at high temperatures (i.e., 850° C. or greater).

Accordingly, there is a continuing need for better, more economical processes and catalysts for the oxidative coupling of methane.

SUMMARY OF THE INVENTION

A discovery has been made that provides a solution to at least some of the problems associated with oxidative coupling of methane reaction. The solution is premised on using a mixed metal oxide material that is capable of promoting the oxidative coupling of methane reaction. The OCM material includes nonporous inert support material having a high thermal conductivity. A mixed metal oxide material is in contact with a surface of the nonporous inert support. The nonporous inert support material is stable in oxidizing atmospheres at high temperature (e.g., up to a 1000° C.). The mixed metal oxide material can be a p-type semiconductor material. Without wishing to be bound by theory, it is believed that use of a p-type semiconductor material allows for oxygen to bind to the catalyst surface and provides longer retention of oxygen at the catalyst site. Thus, a higher ratio of methane to oxygen can be utilized in the reaction. Notably, and as illustrated in a non-limiting manner in the Examples, supporting the mixed metal oxide material on nonporous inert SiC resulted in an unexpected by significant improvement in $C_{2+}$ selectivity and methane conversion with one-fourth of the catalyst amount required.

In one aspect of the invention, supported OCM catalysts are described. A supported OCM catalyst can include (a) a nonporous inert support having a high thermal conductivity, and (b) an OCM mixed metal oxide material in contact with surface of the nonporous inert support. The nonporous support can have a thermal conductivity of 50 to 500 W/m-K, 75 to 300 W/m-K, or 100 to 200 W/m-K. In some aspects, the support can be SiC having a thermal conductivity of 50 to 200 W/m-K, 50 to 150 W/m-K. The nonporous inert support can be in particulate form and has a particle size of 100 to 500 micrometers. The mixed metal oxide material can be adhered to, or coated on, at least a portion of the surface of the nonporous inert support. The mixed metal oxide can form a layer that covers at least a portion of the surface of the nonporous inert support that is 0.1 to up to 100 microns thick, preferably 1 to 50 microns thick. The mixed metal oxide material can be a p-type semiconductor material. In some embodiments, the mixed metal oxide can include at least one lanthanide doped (stabilized) with at least one of a Column 2 metal, a Column 4 metal, a Column 13 metal, or any oxide thereof. Lanthanides can include lanthanum (La), cerium (Ce), ytterbium (Yb), neodymium (Nd), promethium (Pm), samarium (Sm), europium (Eu), gadolinium (Gd), terbium (Tb), dysprosium (Dy), holmium (Ho), erbium (Er), or oxide thereof, or any combination thereof. In some instances, the mixed metal oxide material includes at least two lanthanides. For example, the mixed metal oxide material can include La and Ce where the La:Ce mole ratio is 9:1 to 90:1 or any range or value there between. In other instances, the mixed metal oxide material can include a Column 2 metal and at least one lanthanide metal or oxides thereof. For example, $SrLa_{0.9}Yb_{0.1}Nd_{0.7}O_\delta$, where $\delta$ is a number that varies such that the catalyst is charge neutral can be used as the mixed metal oxide material. In some embodiments, the mixed metal oxide material can be a single phase material. In certain instances, the mixed metal oxide material can have a fluorite type structure, a perovskite type structure, a spinel type structure, a brownmillerite type structure or a pyrochlore type structure. The mixed metal oxide material can include nanoparticles, preferably nanoparticles having a particle size of less 0.1 micrometers (micron) to 10 micrometers, or 0.1 to 0.5 microns. The mixed metal oxide material does not include n-type semiconductor material, preferably a Column 1 metal and/or a Columns 5-12 metal.

In another aspect of the present invention, methods of preparing the OCM catalysts of the present invention are described. A method can include contacting (e.g., at a temperature of 180 to 250° C. or about 200° C.) the mixed metal oxide material with the nonporous inert support to form a supported mixed metal oxide material, and heat-treating (e.g., at a temperature of 350° C. to 1000° C., preferably 400° C. to 900° C.) the supported mixed metal oxide material to form the supported OEM catalyst(s) of the present invention. The mixed metal oxide material can be dispersed in a solvent. The dispersion can be contacted with the inert support material by spraying, coating, or drop coating the dispersion onto the heated inert support material.

In yet another aspect of the present invention, processes for OCM are described. An OCM process can include contacting a reactant feed that includes $CH_4$ with any one of the OCM catalysts of present invention in the presence of an oxidant (e.g., $O_2$ or gaseous elemental sulfur) to produce a product stream that includes $C_{2+}$ hydrocarbons. The OCM catalysts of the present invention are chemically inert with respect to components in the product stream. The OCM reaction operating temperature can be 800° C. to 1000° C., most preferably 850° C. to 900° C. Other components in the product stream can include carbon dioxide ($CO_2$) and carbon monoxide (CO). $C_{2+}$ hydrocarbons can include ethane, ethylene, and $C_3$ and higher hydrocarbons, and mixtures thereof. Selectivity for $C_{2+}$ hydrocarbons can be at least 65%. In a preferred embodiment, the methane conversion remains constant after ignition.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions of the invention can be used to achieve methods of the invention.

The following includes definitions of various terms and phrases used throughout this specification.

The term "inert" is defined as not being chemically reactive. By way of example, the inert support does not react with methane and/or oxygen and the mixed metal oxide material and/or support material does not react with products formed from the oxidative coupling of methane.

The phrase "nonporous" in the context of "nonporous inert support material" refers to solid material that has a density of at least 90%, 91%, 92%, 93%, 94%, 95%, 96%, 97%, 98%, 99%, or a 100% of the material's theoretical density.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %", "vol. %", or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The supported OCM catalysts of the present invention can "comprise," "consist essentially of," or "consist of" particular ingredients, components, compositions, etc. disclosed throughout the specification. With respect to the transitional phrase "consisting essentially of," in one non-limiting aspect, a basic and novel characteristic of the supported OCM catalysts of the present invention are their abilities to catalyze oxidative coupling of methane, preferably at lower reaction temperatures.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

Figure 1A:
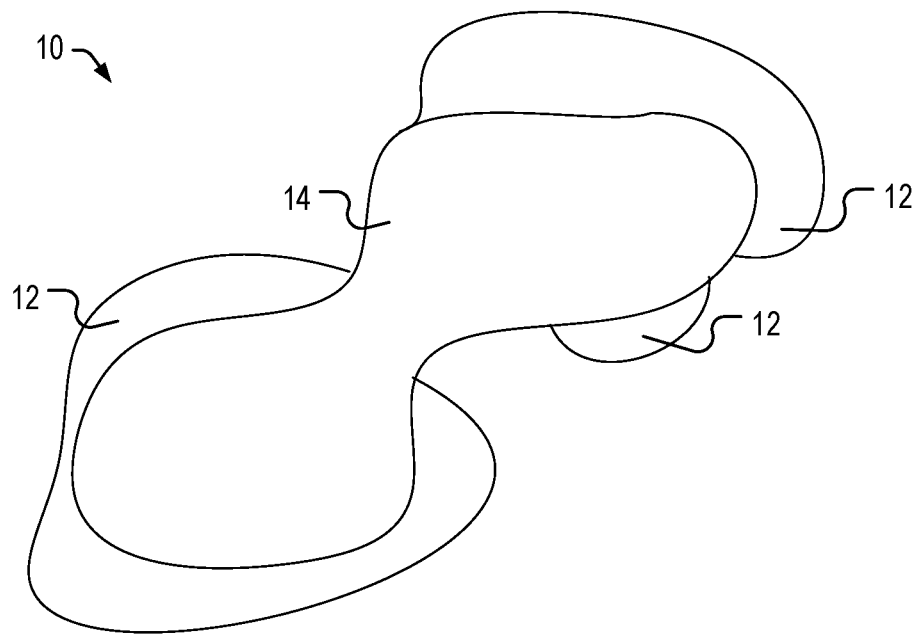
FIG. 1A is an illustration of one example of an OCM material of the present invention that includes a discontinuous layer of a mixed metal oxide material in contact with the nonporous inert support material.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to a least some of the problems associated with the oxidative coupling of methane reaction. The solution is premised on providing a layer of a mixed metal oxide material to the surface of an inert nonporous support having a high thermal conductivity. The mixed metal oxide material can have p-type semiconductor properties, thereby facilitating the abstraction of an electron from each methane molecule to form methyl radicals, which can combine to form $C_{2+}$ hydrocarbons. Since the reaction is exothermic, the use of the inert support having a high thermal conductivity assists in controlling the reaction temperature, thus decreasing the formation of unwanted side products as compared to oxide based supports (low thermal conductivity). Notably, and as illustrated in a non-limiting manner in the examples, the methane conversion remained constant after ignition with high selectivity for ethylene and less amounts of catalysts were required to achieve higher $C_{2+}$ selectivity as compared to unsupported catalysts.

These and other non-limiting aspects of the present invention are discussed in further detail in the following sections with reference to the figures.

A. OCM Catalyst

Figure 1B:
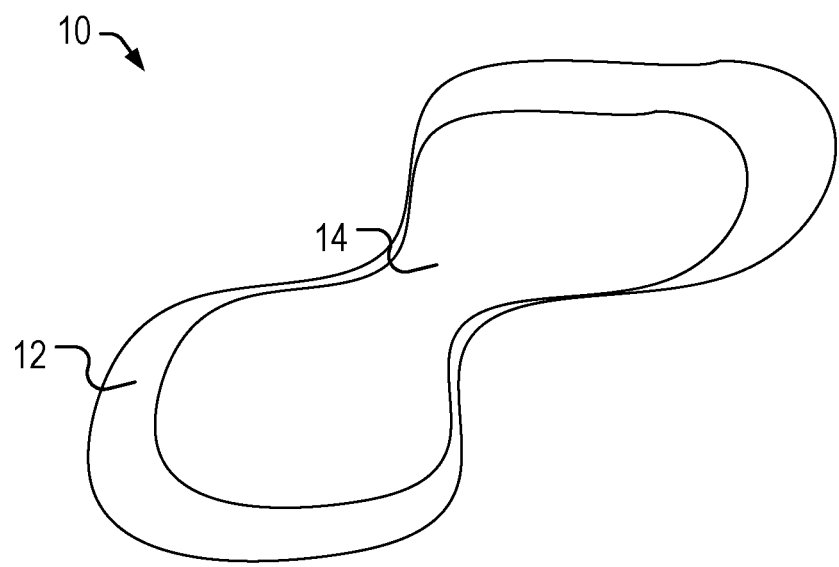
FIG. 1B is an illustration of one example of an OCM material of the present invention that includes a continuous layer of a mixed metal oxide material in contact with the nonporous inert support material.

The OCM catalyst can have nanoparticulate mixed metal oxide material in contact or adhered to the surface of a nonporous inert support material. The nanoparticulate mixed metal oxide material can form a discontinuous layer or continuous layer that coats the nonporous inert support material. The size of the nanoparticles can be from 0.1 nm to 150 nm or at least, equal to, or between any two of 0.1, 1, 10, 20, 30, 40, 50, 60, 70, 80, 90, 100, 110, 120, 130, 140, and 150 nm. The surface, or least a portion of the surface, of the nonporous inert support material can be in contact with the mixed metal oxide material. FIG. 1A is an illustration of the catalyst 10 having discontinuous mixed metal oxide material layers 12 in contact with nonporous inert support material 14. FIG. 1B is an illustration of the catalyst 10 having a continuous mixed metal oxide material layer 12 in contact with nonporous inert support material 14. In certain aspects, at least 50%, 60%, 70%, 80%, 90%, 95%, or 100% the surface area of the nonporous inert support material can be in direct contact with (e.g., coated with) the mixed metal oxide material. The thickness of the mixed metal oxide layer(s) on the surface of the support material can be from 1 to 50 microns, or at least, equal to or between any two of 1, 5, 10, 15, 20, 25, 30, 35, 40, 45 and 50 microns. The mixed metal oxide material can be adhered to the surface of the nonporous inert support through chemical bonding (e.g., a binder present in the mixed metal oxide material or through covalent bonding of the metal oxide with the support). In a preferred embodiment, no layers of other material (e.g., binder material) is between the mixed metal oxide layer and the surface of the support. In some embodiments, a second or more layers can be added to the first layer to form a multi-layered metal oxide material on the nonporous inert support.

1. Nonporous Inert Support Material

The nonporous inert support has a high thermal conductivity. The thermal conductivity of the nonporous inert support can range from 50 to 500 W/m-K, or at least, equal to, or between any two of 50, 75, 100, 125, 150, 175, 200, 225, 250, 275, 300, 325, 350, 375, 400, 425, 450, 475 and 500 W/m-K. Non-limiting examples of nonporous inert support material includes silicon carbide (SiC) and FeCrAlloy (iron, chromium aluminum alloy). SiC can have a thermal conductivity from 50 to 200 W/m-K or at least, equal to, or between any two of 50, 75, 100, 125, 150, 175, and 200 W/m-K. The nonporous inert support can have a density of 3.0 to 3.2 g/mL or any value or range there between and can be of any shape (e.g., spherical, pellet, elliptical). The nonporous inert support does not include, or has substantially few (e.g., less than 0.5%) pores. The nonporous inert support material can have a particle size of 300 to 500 micron, or about 350 to 400 microns.

2. Mixed Metal Oxide Material

The mixed metal oxide material can be a compound or a mixture of compounds that includes two or more oxidized metals and oxygen. For example, a mixed metal oxide material can include or be a compound having a formula of $M1_xM2_yO_\delta$, wherein M1 and M2 are the same or different metal elements, O is oxygen and x and y are numbers from 0.01 to 100 and $\delta$ is a number that varies such that the composition is charge neutral. As more metals are added the formula is expanded. For example, if three are included, the formula is $M1{\times}M2_yM3_zO_\delta$, where x, y, and z are numbers from 0.01 to 100 and $\delta$ is a number that varies such that the composition is charge neutral and M3 is the 3 metal. The same process is applied if 4, 5, 6, etc. metals are used. A mixed metal oxide material can include metal elements in various oxidation states and can include more than one type of metal element. In some embodiments, the mixed metal oxide material includes oxy-hydroxide materials. An oxy-hydroxide material is $M1{\times}M2_yO_zOH$, where M1 and M2 are a metal element, O is oxygen, OH is hydroxy, and x, y and z are numbers from 1 to 100. The OCM catalyst of the present invention can include up to 30 wt. % of total metal and/or metal oxide, or from 0.1 wt. % to 30 wt. %, from 1 wt. % to 20 wt. %, from 5 wt. % to 25 wt. % or from 3 wt. % to 7 wt. % and all wt. % there between. The balance can be the nonporous inert support.

The mixed metal oxide material can include metals from the Lanthanide series or Columns 2, 4, 13, and 14 of the Periodic Table, or any oxide thereof. By way of example, the mixed metal oxide material can be a combination of two or more lanthanides or oxides thereof, at least one Column 2 metal and at least one lanthanide metal or oxides thereof. Non-limiting examples of lanthanides include lanthanum (La), cerium (Ce), ytterbium (Yb), niobium (Nb), Samarium (Sa), Europium (Eu), gadolinium (Gd), terbium (Tb), dysprosium (Dy), holmium (Ho), and erbium (Er). Non-limiting examples of Column 2 elements include magnesium (Mg), calcium (Ca), strontium (Sr), and barium (Ba). Non-limiting examples of Columns 4, 13, and 14, metals include titanium (Ti), zirconium (Zr), gallium (Ga), indium (In), germanium (Ge), and tin (Sn). In some embodiments, the mixed metal oxide material is a single phase structure. The mixed metal oxide material can have a fluorite structure, a perovskite type structure, a spinel type structure, a brownmillerite type structure or a pyrochlore type structure.

Non-limiting examples of mixed metal oxide materials include $LaCeO_\delta$, $Mg_{0.1}Zr_{0.9}O_\delta$, $SrLa_{0.9}Yb_{0.1}Nd_{0.7}O_6$, where $\delta$ is a number that varies such that the catalyst is charge neutral, and $MnWO_4$. The La:Ce molar ratio can be 9:1 to 99:1, or at least, equal to, or between any two of 9:1, 10:1, 20:1, 30:1, 40:1, 50:1, 60:1, 70:1, 80:1 90:1, and 99:1. In some embodiments, the mixed metal oxide material can be an aliovalently doped fluorite catalyst, (e.g., india stabilized zirconia (ISZ or InZrO)). By substituting +3 valence ion ($M^{1+3}$) for one of the +4 valent $M^{2+4}$ (e.g., Zr, Ti, or Ce) ions in $M^2O_2$ crystal lattice, an oxygen vacancy can be created. By way of example, $In^{+3}$ can be substituted for a $Zr^{+4}$ atom in the crystal structure of zirconia, thus forming one or more oxygen vacancies. The oxygen vacancy can participate actively in the oxidative coupling of methane reaction. The catalyst can have a single crystal structure (as determined by known crystallography methods such as XRD), which allows the catalyst to have more oxygen vacancies, thus providing an increase in catalyst activity as compared to catalyst having a metal impregnated in a support.

The metal oxide material can be prepared from metal oxides or metal oxide precursor materials using known metal oxide preparation methodology. Non-limiting examples of metal oxide precursor materials include metal nitrates, metal nitrate hydrates, metal nitrate trihydrates, metal nitrate hexahydrates, and metal nitrate nonahydrates. A non-limiting example of a commercial source of the above mentioned metals or metal precursors is MilliporeSigma (U.S.A.) or Alpha Aesar (U.S.A.). Non-limiting examples of preparation methods for the mixed metal oxide material catalysts are known to those having ordinary skill in the catalyst chemistry. For example the mixed metal oxide material can be prepared by any one of the methods such as liquid-liquid blending, solid-solid blending, or liquid-solid blending (i.e., any of precipitation, co-precipitation, impregnation, complexation, gelation, crystallization, microemulsion, sol-gel, solvothermal, hydrothermal, sonochemical, or combinations thereof), glycine-nitrate propellant chemistry methodology, and the like.

B. Preparation of OCM Catalyst of the Present Invention

The mixed metal oxide material can be contacted with the nonporous inert support using a variety of techniques to form a supported mixed metal oxide material. Contacting can include preparing a suspension, or dispersion, of the mixed metal oxide material suspended or dispersed in a solvent. As used herein suspension and dispersion are used interchangeably. Solvents can include alcohols (e.g., ethanol, n-butanol, propanol, or mixtures thereof), ethers, hydrocarbons, or mixtures, or blend thereof. The dispersion can include optional ingredients. Optional ingredients can include binders (e.g., poly(vinyl butyral), surfactants (e.g., fatty acids or mixtures thereof (e.g., menhaden fish oil)), and the like. The amount of binder can range from 0.1 to 10 wt. % or any value there between (e.g., 0.1, 1, 2, 3, 4, 5, 6, 7, 8 9 and 10 wt. %) based on the total amount of mixed metal oxide. The amount surfactant can range from 0.1 to 5 wt. %, or any value there between (e.g., 0.1, 1, 2, 3, 4, and 5 wt. %) based on the total amount of mixed metal oxide. The amount of catalyst, solvent, and optional ingredients can be varied to obtain a dispersion having well dispersed materials. By way of example, a dispersion can includes 20 wt. % to 50 wt. % of mixed metal oxide material, 38 wt. % to 77 wt. % solvent, and 3 wt. % to 12 wt. % optional additives. In one instance, the dispersion can include 20 wt. % to 50 wt. % of mixed metal oxide material, 2 wt. % to 8 wt. % binder, and 1 to 4 wt. % surfactant. In some embodiments, the solvent can be a mixture of solvents. For example, a solvent mixture can include 50 to 80 wt. % of a lower boiling solvent (e.g., ethanol) and 20 to 50 wt. % of a higher boiling solvent (n-butanol), or 60 to 75 wt. % of the lower boiling solvent and 25 wt. % to 40 wt. % of the higher boiling solvent. In one instance, the dispersion can consist of, or consist essentially of, 20 wt. % to 50 wt. % of mixed metal oxide material, 2 wt. % to 8 wt. % binder, and 1 to 4 wt. % surfactant with the balance being solvent. The mixed metal oxide particles in the dispersion can be milled to reduce the mixed metal oxide material particle size to provide a particle size distribution adequate for application to the nonporous inert support. Milling can include ball milling, attrition milling, and the like. The resulting dispersion can have a monomodal, bimodal, or trimodal particle size distribution. The particle size of the mixed metal oxide material can have at least 90% of the particle size distribution below 150 nm. The size of the nanoparticles can be from 0.1 nm to 150 nm or at least, equal to, or between any two of 0.1, 1, 10, 20, 30, 40, 50, 60, 70, 80, 90, 100, 110, 120, 130, 140, and 150 nm.

The nonporous inert support can be heated to a temperature of 180° C. to 250° C., or at least, equal to, or between any two of 180° C., 185° C., 190° C., 200° C., 205° C., 210° C., 215° C., 220° C., 225° C., 230° C., 235° C., 240° C., 245° C., and 250° C., or about 200° C. The dispersion can be applied to (contacted with) the heated nonporous inert support using known application methodology such as spraying coating or drop coating the dispersion onto the heated inert support material. In some embodiments, the dispersion can be heated prior to contacting. In some embodiments, the dispersion and/or support material are not heated. In yet another embodiment, the dispersion is heated and the support material is not heated. During contacting the nonporous inert support material can be agitated so that the mixed metal oxide dispersion at least partially coats the nonporous inert support material. In some embodiments, at least 50%, 60%, 70%, 80%, 90% or 100% or any range or value there between of the nonporous inert support material surface is in contact with the mixed metal oxide material. Such contact can produce a continuous or discontinuous layer of mixed metal oxide material dispersed on the surface of the nonporous inert support material. As the dispersion is contacted, the solvent can evaporate, and/or the contacted support material can be heated at a higher temperature to remove the solvent. After the solvent is removed the coated support material can be heat-treated in the presence of an oxidizing source (e.g., air, or oxygen enriched air) at a temperature of 350° C. to 1000° C., or at least, equal to, or between any two of 350° C., 400° C., 450° C., 500° C., 550° C., 600° C., 650° C., 700° C., 750° C., 800° C., 850° C., 900° C., 950° C., and 1000° C. to produce the OCM catalyst material of the present invention. In one instance, the heat-treating temperature is 400° C. to 900° C., or about 800° C. After cooling to 20 to 35° C. the OCM catalyst material can be collected and stored. Prior to use, the OCM catalyst material can be reduced in size, and/or pelletized prior to use.

C. Reactants

The reactant mixture in the context of the present invention can be a gaseous mixture that includes, but is not limited to, a hydrocarbon or mixtures of hydrocarbons and oxygen. The hydrocarbon or mixtures of hydrocarbons can include natural gas, liquefied petroleum gas containing of $C_2$-$C_5$ hydrocarbons, $C_6$+ heavy hydrocarbons (e.g., $C_6$ to $C_{24}$ hydrocarbons such as diesel fuel, jet fuel, gasoline, tars, kerosene, etc.), oxygenated hydrocarbons, and/or biodiesel, alcohols, or dimethyl ether, or combinations thereof. In a preferred aspect, the hydrocarbon is a mixture of hydrocarbons that is predominately methane (e.g., natural gas). The oxygen containing gas used in the present invention can be air, oxygen enriched air, or oxygen gas. The reactant mixture may further contain other gases, provided that these do not negatively affect the reaction. Examples of such other gases include carbon dioxide, nitrogen, and hydrogen. The hydrogen may be from various sources, including streams coming from other chemical processes, like ethane cracking, methanol synthesis, or conversion of methane to aromatics. Carbon dioxide can be obtained from natural gas or from a waste or recycle gas stream (e.g., from a plant on the same site, like for example from ammonia synthesis).

D. Oxidative Coupling of Methane Process

The reaction processing conditions can be varied as desired. In one non-limiting aspect, the reaction processing conditions can include contacting a feed stream comprising hydrocarbon(s) and oxidant(s) with any of the catalysts described throughout the specification under specifically selected OCM conditions (e.g., methane to oxygen ratio of 7.4 and a reaction temperature of 340 to 1000° C.). This can result in a methane conversion of greater than 15% and a $C_{2+}$ selectivity of at least 65%. In one aspect of the present invention, the methane to oxygen ratio can be 7.4 and the light off temperature can be 340° C. to 375° C. or about 350° C. In some embodiments, the reaction temperature can be about 425 to 500° C. and methane conversion is 18% or more, 19% or more, and 20% or more. In another aspect, the $O_2$ conversion can be 98% or more, and preferably 99% or more at 375° C. In another aspect the $C_{2+}$ selectivity can be 65% or more, 79% or more, and preferably 80% or more. In some preferred embodiments, the sum of the $CH_4$ conversion percentage and the $C_{2+}$ hydrocarbon selectivity percentage can be 100 or more. As described in more detail below, the methane to oxygen ratio, reaction temperature, and other processing parameters can be modified as desired.

In one aspect of the invention, the catalyst of the present invention can be used in continuous flow reactors to produce $C_{2+}$ hydrocarbons from methane (e.g., natural gas). Non-limiting examples of the configuration of the catalytic material in a continuous flow reactor are provided throughout this specification. The continuous flow reactor can be a fixed bed reactor, a stacked bed reactor, a fluidized bed reactor, or an ebullating bed reactor. In a preferred aspect of the invention, the reactor can be a fixed bed reactor. The catalytic material can be arranged in the continuous flow reactor in layers (e.g., catalytic beds).

Processing conditions in the continuous flow reactor may include, but are not limited to, temperature, pressure, oxidant source flow (e.g., air or oxygen), hydrocarbon gas flow (e.g., methane or natural gas), ratio of reactants, or combinations thereof. Process conditions can be controlled to produce $C_{2+}$ hydrocarbons with specific properties (e.g., percent ethylene, percent butene, percent butane, etc.). The average temperature in the continuous flow reactor can be 795° C., 800° C., 805° C., 810° C., 815° C., 820° C., 825° C., 830° C., 835° C., 840° C., 845° C., 850° C., 860° C., 870° C., 880° C., 890° C., 900° C., 925° C., 950° C., 975° C., or 1000° C., or any value or range there between. Pressure in the continuous flow reactor can range about 0.1 MPa to 0.5 MPa. The gas hourly space velocity (GHSV) of the reactant feed can range from 500 $h^{-1}$ to 1,000,000 $h^{-1}$ or more. In some embodiments, the GHSV can be as high as can be obtained under the reaction conditions. In some aspects of the present invention, the reactant mixture can have a molar ratio of methane to oxygen ranges from 4 to 20, 5 to 15, or 5 to 7.5 or any range there between. The molar ratio of methane to oxygen can be 4, 4.5, 5, 5.5, 6, 6.5, 7, 7.5, 8, 8.5, 9, 9.5, 10, 15, or 20 or any value there between. Severity of the process conditions may be manipulated by changing the hydrocarbon source, oxygen source, pressure, flow rates, the temperature of the process, the catalyst type, and/or catalyst to feed ratio. In a preferred embodiment, the average temperature ranges from about 800° C. to about 1100° C., and more preferably from about 900° C. to 1000° C. or any range there between, a pressure at 0.1 to 0.5 MPa and/or a GHSV from about from 500 to 200,000 $h^{-1}$ or more.

Figure 2:
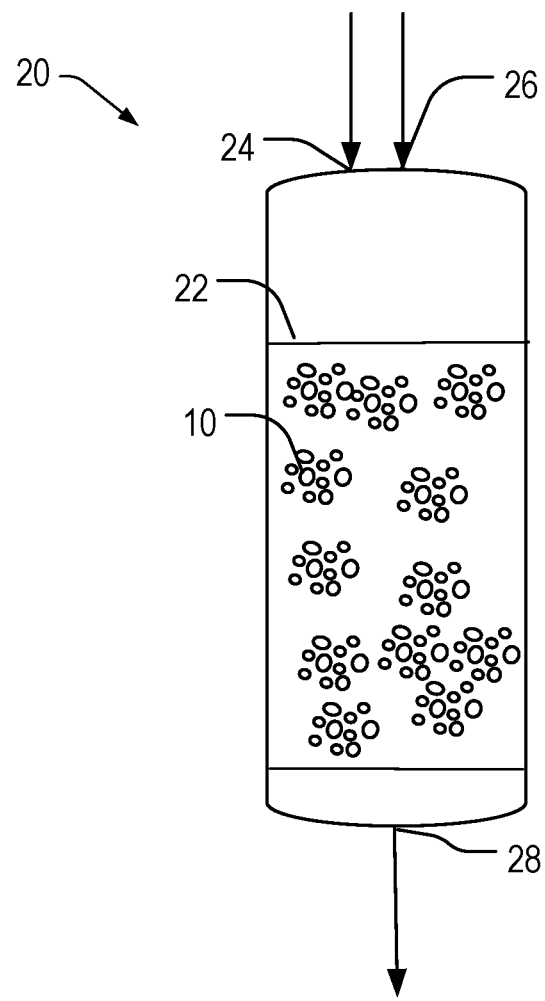
FIG. 2 is an illustration of a system to produce $C_{2+}$ hydrocarbons using the OCM of the present invention.

Referring to FIG. 2, a schematic of system 20 for the production of $C_{2+}$ hydrocarbons is depicted. System 20 can include a continuous flow reactor 22 and the supported OCM catalyst material 10. A reactant stream that includes methane can enter the continuous flow reactor 22 via the feed inlet 24. An oxygen containing gas (oxidant) can be provided via oxidant source inlet 26. In some aspects of the invention, methane and the oxygen containing gas are fed to the reactor via one inlet. The reactants can be provided to the continuous flow reactor 22 such that the reactants mix in the reactor to form a reactant mixture prior to contacting the catalyst 10. In some embodiments, the catalytic material and the reactant feed can be heated to approximately the same temperature. In some instances, the catalyst 10 may be layered in the continuous flow reactor 22. Contact of the reactant mixture with the catalyst 10 produces a product stream (for example, $C_{2+}$ hydrocarbons and generates heat (i.e., an exotherm or rise in temperature is observed). The product stream can exit continuous flow reactor 22 via product outlet 28.

Figure 3:
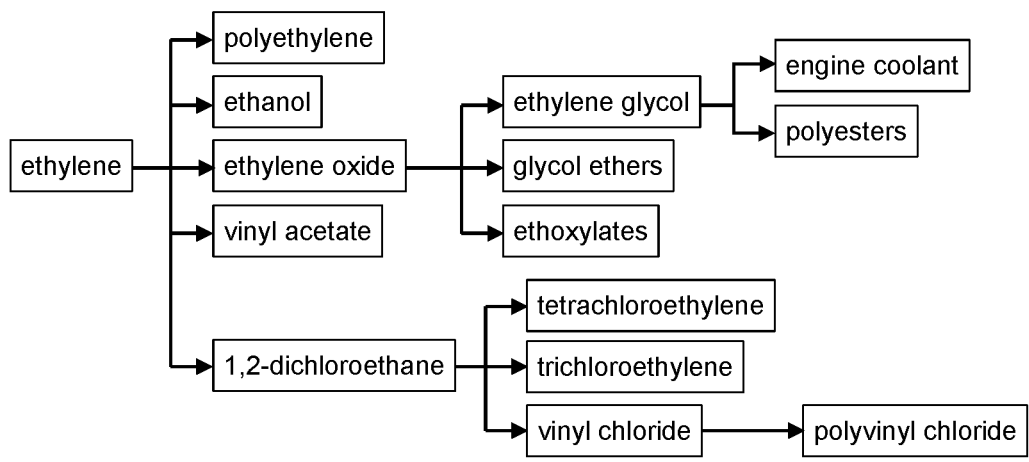
FIG. 3 is an illustration of the products that can be made using ethylene as a starting material.

The resulting product stream having $C_{2+}$ hydrocarbons can be separated using gas/liquid separation techniques (e.g., distillation, absorption, membrane technology, etc.) to produce gaseous streams that include carbon monoxide, carbon dioxide, unreacted methane, hydrogen, $C_{2+}$ hydrocarbons product, and/or water. In a particular instance, the $C_{2+}$ hydrocarbons can be separated from hydrogen and carbon monoxide and/or carbon dioxide, if present, using gas/gas separation techniques (e.g., a hydrogen selective membrane, a carbon monoxide selective membrane, or cryogenic distillation) to produce streams of $C_{2+}$ hydrocarbons, carbon monoxide, carbon dioxide, hydrogen, or mixtures thereof. The resulting streams can be used in additional downstream reaction schemes to create additional products or for energy production. Examples of other products include chemical products such as methanol production, olefin synthesis (e.g., via Fischer-Tropsch reaction), aromatics production, carbonylation of methanol, carbonylation of olefins, the reduction of iron oxide in steel production, etc. The resulting streams can further be isolated and/or stored for later use. By way of example, FIG. 3 provides non-limiting examples of various chemicals that can be made from ethylene.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Supported LaCeO Material of the Present Invention

A LaCe oxide material having a La:Ce molar ratio of 15:1 was prepared by co-precipitation. The LaCe oxide material was incorporated into a coating suspension having the composition shown in Table 1.

TABLE 1

|  | Composition (wt. %) |
|---|---|
| Mixed Metal Oxide Material | 30.00 |
| Menhaden Fish Oil | 1.5 |
| n-Butanol | 16.38 |
| Ethanol, anhydrous | 49.13 |
| Poly(vinyl butyral) B-98 | 3.00 |
| Total | 100. |

Figure 4:
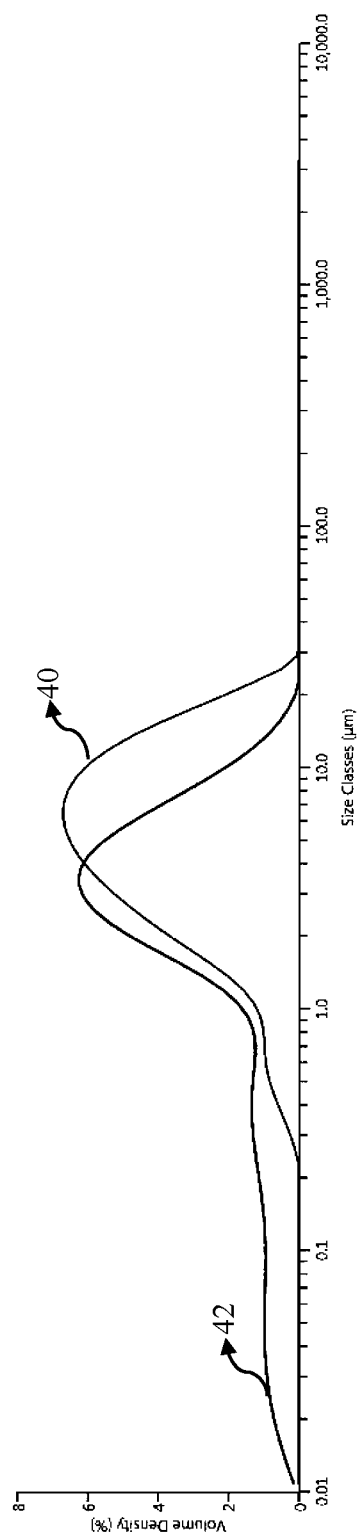
FIG. 4 is a particle size distribution for milled LaCe oxide material on nonporous inert SiC particles after 1 and 2 hours of milling.

The suspension was milled in a jar mill for 2 hours at 30 RPM, after which time the particle size distribution shown in FIG. 4 was obtained. Data line 40 is after 1 hour and data line 42 is after 2 hours. A portion of the milled LaCe suspension (about 5 g) was added to SiC chips (about 5 g, Alfa Aesar (USA), 46 grit) in a rotory evaporator flask. The solvent was removed from the LaCe supsension as the flask turned in a warm oil bath (about 75° C.). During removal of the solvent, some of the LaCe material coated the sides of the flask. After the solvent was removed, the entire contents of the flask were remove, dried fully, and sieved to remove catalyst powder not associated with the SiC chips. The catalyst was then calcined at 600° C. for 10 hours. The resulting catalyst contained about 12.5 wt. % LaCe oxide material.

Example 2

Synthesis of Supported LaCeO Material of the Present Invention

SiC chips (about 5 g, Alfa Aesar (USA), 46 grit) were placed in a glazed, wide-mouth crucible, which was placed on a hotplate set for 200° C. Once the SiC chips were heated, a portion of the milled LaCe suspension (about 1.5 g) from Example 1 was added slowly (a few drops at a time) by pipette while stirring the chips with a stainless steel spatula. This procedure distributed the LaCe oxide material evenly as the solvent evaporated and resulted in less LaCe oxide material depositing on the walls of the crucible compared to Example 1. Stirring was continued until all of the solvent had vaporized before the addition of more suspension. After all the suspension had been added, the catalyst was then calcined at 600° C. for 10 hours. The resulting catalyst contained about 10 wt. % LaCe oxide material. The sample was more homogeneous than that prepared in Example 1 as determined by visual inspection.

Example 3

Figure 5:
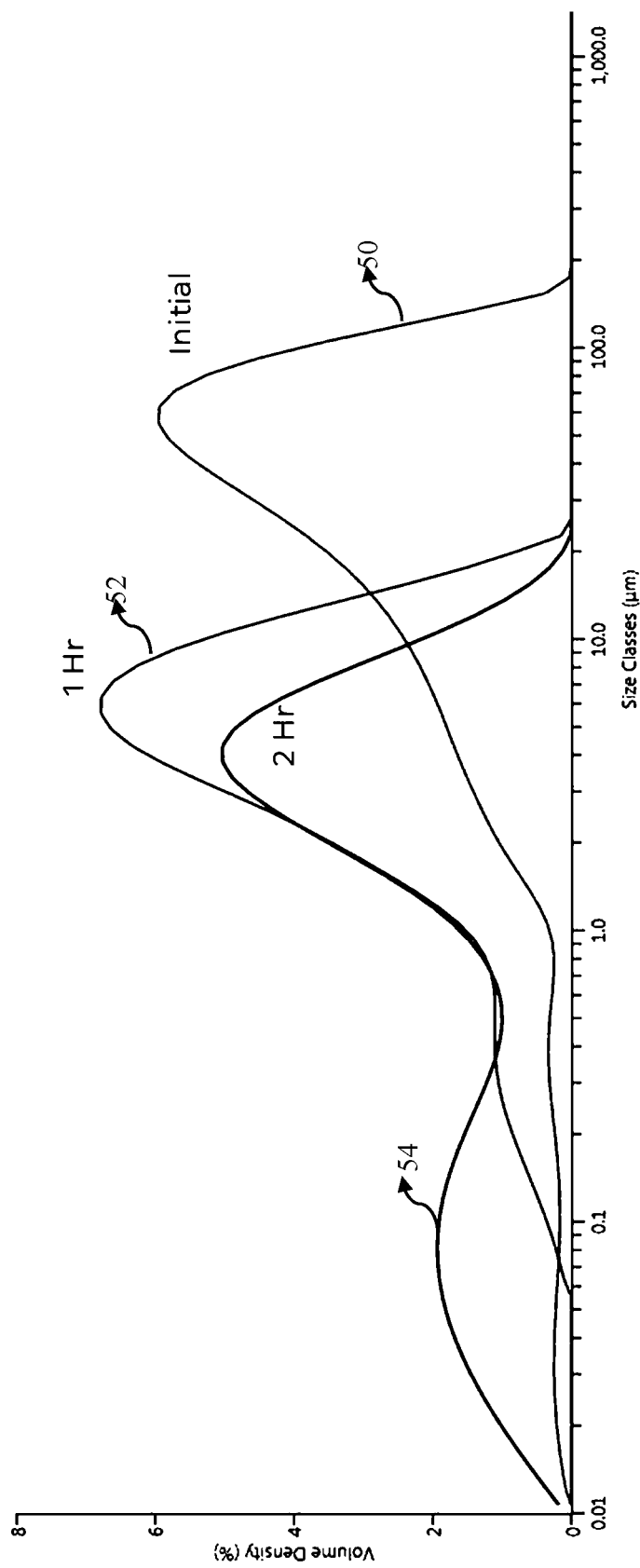
FIG. 5 is a particle size distribution for native $SrLa_{0.9}Yb_{0.1}Nd_{0.7}O_6$ on nonporous inert SiC particles and milled $SrLa_{0.9}Yb_{0.1}Nd_{0.7}O_6$ on nonporous inert SiC particles after 1 and 2 hours of milling.

Synthesis of Supported $SrLa_{0.9}Yb_{0.1}Nd_{0.7}O_\delta$ Material of the Present Invention A $SrLa_{0.9}Yb_{0.1}Nd_{0.7}O_\delta$ material was prepared by co-precipitation and calcined at 300° C. The material was incorporated into a coating suspension having the composition shown in Table 1. The suspension was milled in a jar mill for 2 hours at 30 RPM, after which time the particle size distribution shown in FIG. 5 was obtained. Data line 50 the initial particle size distributions, data line 52 is after 1 hour and data line 54 is after 2 hours. From the data, it was determined that longer milling times produced a bimodal particle distribution. A portion of the milled material was added to SiC chips using the procedure of Example 2. The resulting catalyst contained about 11 wt. % $SrLa_{0.9}Yb_{0.1}Nd_{0.7}O_\delta$ material.

Example 4

Synthesis of Nonporous Inert Supported $Mg_{0.1}Zr_{0.9}O_\delta$ Material of the Present Invention A $Mg_{0.1}Zr_{0.9}O_\delta$ material was prepared using the glycine-nitrate procedure described by Jain et al. (*Combustion and Flame*, 1981, 40, pp. 71-79) and then sintered at 1,000° C. for 6 hours. The sintered material was mixed with the SiC chips, and the dry mixture was shaken to homogenize at room temperature (about 20° C. to 30° C.). After some shaking, acetone (about 1 mL) was added dropwise to the bottle and stirred with a spatula to further homogenize the mixture. After evaporation of the acetone, the material was dried in an oven at 115° C. to remove the remaining acetone. using the procedure of Example 2. The resulting catalyst contained about 20 wt. % $Mg_{0.1}Zr_{0.9}O_\delta$ material on silicon carbide.

Comparative Example 5

Oxidative Coupling of Methane Using Unsupported LaCeO Material

Figure 6:
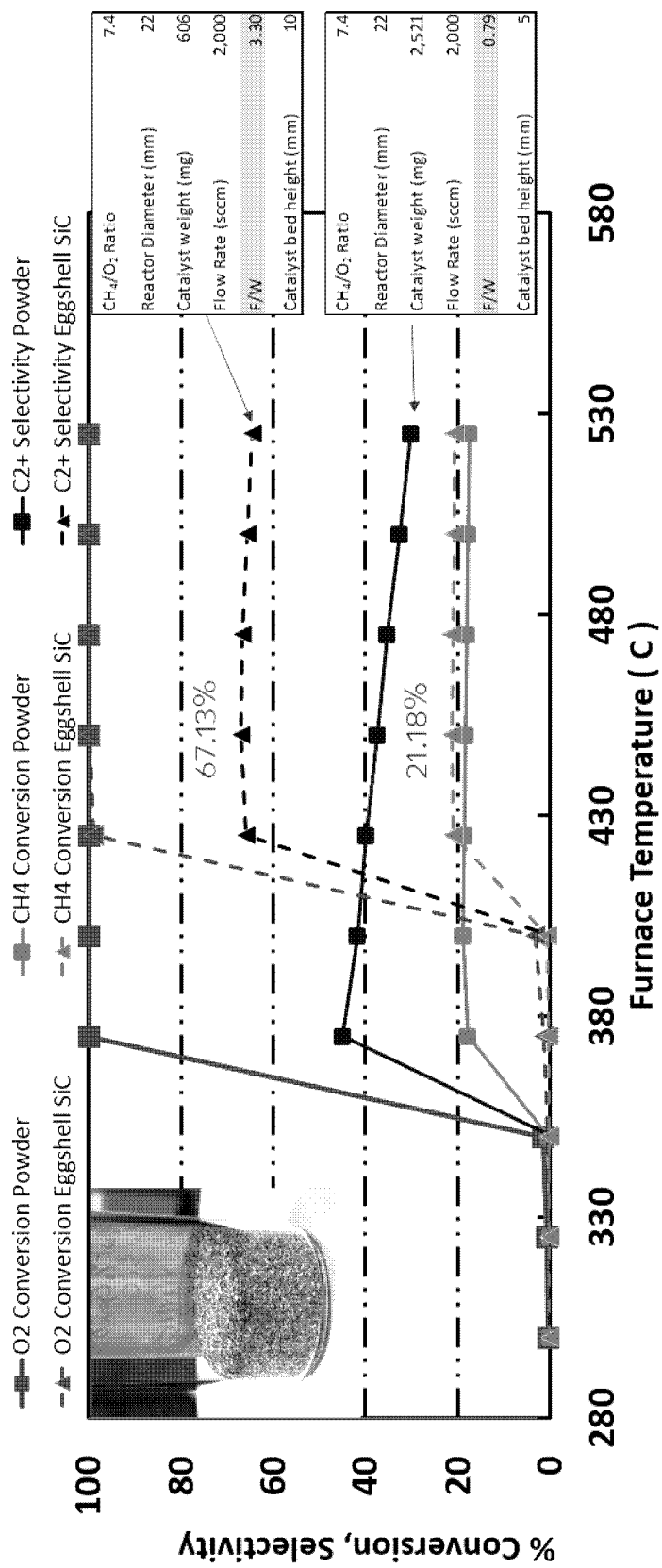
FIG. 6 is a graphical representation of the OCM reaction using comparative unsupported LaCe oxide material and supported LaCe oxide material of the present invention.

The unsupported LaCeO material of Example 1 was compacted in a cold isostatic press to 15,000 psig and then ground and sized to 40/60 mesh. The compacted material (about 2.52 g) was loaded into a 22 mm ID quartz tube reactor supported by quartz wool and quartz chips. The catalyst bed height was 5 mm. The tube was mounted into a single zone furnace with the catalyst in the center of the heated zone; and the furnace was ramped from 300° C. to 525° C. in 25° C. increments. At each temperature, gas samples were taken and components were measured by gas chromatography. (Agilent 7890 GC with flame ionization detector (FID) and an alumina PLOT column for the hydrocarbons and a thermal conductivity detector (TCD) plus mole sieve column for the permanent gases). Oxygen conversion, methane conversion and selectivity to $C_{2+}$ compounds were calculated and plotted. FIG. 6 shows data for the unsupported (solid lines) material. From the data, it was determined that light off occurred at about 350° C. and 100% oxygen conversion was obtained at 375° C. Maximum methane conversion was 18.7% and maximum $C_{2+}$ selectivity was 44.9%, which declined after ignition.

Example 6

Oxidative Coupling of Methane Using Supported LaCeO Material of the Present Invention The nonporous inert supported 10 wt. % LaCeO material of Example 2 was tested as described in Example 5 except that the catalyst was not compacted and the catalyst bed was 10 mm in height and the total amount of catalyst was reduced (0.606 gm, or about 24% of the catalyst in Example 5). FIG. 6 shows data for the supported catalyst (dotted lines) of the present invention. From the data, it was determined that light off was delayed by about 50° C., but unexpectedly, the maximum $C_{2+}$ selectivity increased to 67.13%, which is a 50% increase over the unsupported catalyst. The maximum methane conversion increased to 21.18% (an increase of 13%). In addition, the $C_{2+}$ selectivity exhibited a plateau from 425 to 500° C., whereas the selectivity for the unsupported catalyst decreased immediately on ignition. Thus, supporting the mixed metal oxide material on SiC resulted in an unexpected significant improvement in $C_{2+}$ selectivity and methane conversion with one-fourth of the catalyst required.

Comparative Example 7

Figure 7:
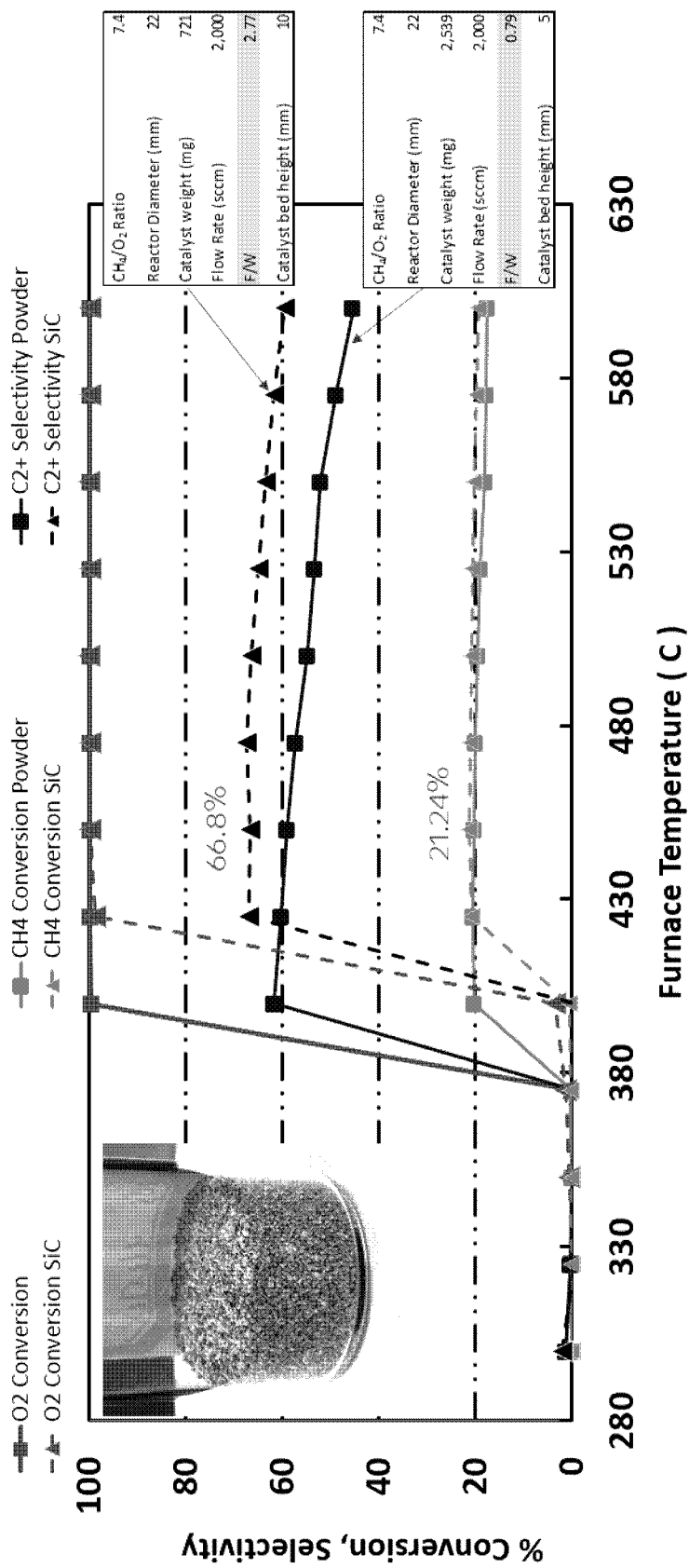
FIG. 7 is a graphical representation of the OCM reaction using comparative unsupported $SrLa_{0.9}Yb_{0.1}Nd_{0.7}O_\delta$ material and supported $SrLa_{0.9}Yb_{0.1}Nd_{0.7}O_\delta$ material of the present invention.

Oxidative Coupling of Methane Using Unsupported $SrLa_{0.9}Yb_{0.1}Nd_{0.7}O_\delta$ Material The nonporous inert supported $SrLa_{0.9}Yb_{0.1}Nd_{0.7}O_\delta$ material of Example 3 was compacted in a cold isostatic press to 15,000 psig and then ground and sized to 40/60 mesh. The compacted material (about 2.54 g) was tested per the procedure of Example 5. FIG. 7 shows data for the unsupported (solid lines) material. From the data, it was determined that light occurred at about 375° C. and 100% oxygen conversion was obtained at 400° C. Maximum methane conversion was 20.6% and maximum $C_{2+}$ selectivity was 61.7%.

Example 8

Oxidative Coupling of Methane Using Supported $SrLa_{0.9}Yb_{0.1}Nd_{0.7}O_\delta$ Material of the Present Invention The nonporous inert supported $SrLa_{0.9}Yb_{0.1}Nd_{0.7}O_\delta$ material of Example 3 was tested as described in Example 7 except that catalyst bed was 10 mm in height, the catalyst was not compacted, and the total amount of catalyst was reduced (0.721 gm, or about 28% of the catalyst in Example 6). FIG. 7 shows data for the supported catalyst (dotted lines) of the present invention. From the data, it was determined that light off was delayed by about 25° C., but unexpectedly, the maximum $C_{2+}$ selectivity increased to 66.8%, which is a 8% increase over the unsupported catalyst. The maximum methane conversion increased to 21.18% (an increase of 2.4%). In addition, the $C_{2+}$ selectivity exhibited a plateau from 425 to 500° C., whereas the selectivity for the unsupported catalyst decreased immediately on ignition. Thus, supporting the mixed metal oxide material on dense SiC resulted in an unexpected by significant improvement in $C_{2+}$ selectivity and methane conversion with one-fourth of the catalyst required.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A supported oxidative coupling of methane (OCM) catalyst comprising:
   a nonporous inert support having a high thermal conductivity; and
   an OCM mixed metal oxide material in contact with a surface of the nonporous inert support;
   wherein the nonporous inert support has a thermal conductivity of 55 to 500 W/m-K; and
   wherein the nonporous inert support is in particulate form and has a particle size of 300 to 500 micrometers.

2. The supported OCM catalyst of claim 1, wherein the OCM mixed metal oxide material is a p-type semiconductor material.

3. The supported OCM catalyst of claim 1, wherein the nonporous inert support has a thermal conductivity of 75 to 300 W/m-K.

4. The supported OCM catalyst of claim 1, wherein the nonporous inert support comprises nonporous silicon carbide.

5. The supported OCM catalyst of claim 4, wherein the silicon carbide has a thermal conductivity of 50 to 200 W/m-K.

6. The supported OCM catalyst of claim 1, wherein the nonporous inert support has a thermal conductivity of 100 to 200 W/m-K.

7. The supported OCM catalyst of claim 1, wherein the OCM mixed metal oxide material forms a layer that covers at least a portion of the surface of the nonporous inert support, and wherein the metal oxide layer is from 0.1 to up to 100 microns thick.

8. The supported OCM catalyst of claim 1, wherein the OCM mixed metal oxide material comprises at least one lanthanide doped with at least one of a Column 2 metal, a Column 4 metal, a Column 13 metal, or any oxide thereof.

9. The supported OCM catalyst of claim 1, wherein the OCM mixed metal oxide comprises a lanthanide doped with a column 2 metal.

10. The supported OCM catalyst of claim 9, wherein the lanthanide is selected from the group consisting of lanthanum (La), cerium (Ce), ytterbium (Yb), neodymium (Nd), promethium (Pm), samarium (Sm), europium (Eu), gadolinium (Gd), terbium (Tb), dysprosium (Dy), holmium (Ho) and erbium (Er), or oxides thereof, or any combination thereof.

11. The supported OCM catalyst of claim 9, wherein the a Column 2 metal is strontium.

12. The supported OCM catalyst of claim 9, wherein the silicon carbide is nonporous and has a thermal conductivity of 50 to 200 W/m-K.

13. The supported OCM catalyst of claim 1, wherein the nonporous inert support comprises silicon carbide.

14. The supported OCM catalyst of claim 13, wherein the OCM mixed metal oxide material has a fluorite type structure, a spinel type structure, a brownmillerite type structure or a pyrochlore type structure.

15. The supported OCM catalyst of claim 1, wherein OCM the mixed metal oxide material comprises nanoparticles having a particle size of 0.1 micrometers to 10 micrometers.

16. The supported OCM catalyst of claim 1, wherein the OCM mixed metal oxide material does not include n-type semiconductor material.

17. The supported OCM catalyst of claim 1, wherein the nonporous inert support is in particulate form and has a particle size of 300 to 500 micrometers.

18. A supported oxidative coupling of methane (OCM) catalyst comprising:
a nonporous inert support having a high thermal conductivity; and
an QCM mixed metal oxide material in contact with a surface of the nonporous inert support;
wherein the nonporous inert support has a thermal conductivity of 55 to 500 W/m-K and wherein the OCM mixed metal oxide material comprises $SrLa_{0.9}Yb_{0.1}Nd_{0.7}O_\delta$, where $\delta$ is a number that varies such that the catalyst is charge neutral.

19. A method of preparing the oxidative coupling of methane (OEM) catalyst of claim 1, the method comprising:
contacting the OCM mixed metal oxide material with the nonporous inert support to form a supported OCM mixed metal oxide material; and
heat-treating the supported OCM mixed metal oxide material under conditions sufficient to form the supported OEM catalyst.

20. A process for the oxidative coupling of methane (OCM), the process comprising contacting a reactant feed comprising methane (CH4) with the OCM catalyst of claim 1 in the presence of an oxidant to produce a product stream comprising $C_{2+}$ hydrocarbons.

* * * * *